(12) United States Patent
Sullivan et al.

(10) Patent No.: US 11,013,641 B2
(45) Date of Patent: May 25, 2021

(54) GARMENT FOR DETECTING ABSORBENT ARTICLE LEAKAGE AND METHODS OF DETECTING ABSORBENT ARTICLE LEAKAGE UTILIZING THE SAME

(71) Applicant: Kimberly-Clark Worldwide, Inc., Neenah, WI (US)

(72) Inventors: Shawn Jeffery Sullivan, Neenah, WI (US); Davis Dang H. Nhan, Menasha, WI (US); Rebecca E. Strong, Appleton, WI (US); Andrew Long, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 16/500,116

(22) PCT Filed: Apr. 5, 2017

(86) PCT No.: PCT/US2017/026034
§ 371 (c)(1),
(2) Date: Oct. 2, 2019

(87) PCT Pub. No.: WO2018/186842
PCT Pub. Date: Oct. 11, 2018

(65) Prior Publication Data
US 2020/0375809 A1 Dec. 3, 2020

(51) Int. Cl.
*A61F 13/42* (2006.01)
*A61F 13/74* (2006.01)
*A61F 13/84* (2006.01)

(52) U.S. Cl.
CPC .............. *A61F 13/42* (2013.01); *A61F 13/74* (2013.01); *A61F 13/84* (2013.01); *A61F 2013/424* (2013.01); *A61F 2013/8482* (2013.01)

(58) Field of Classification Search
CPC .......... A61F 13/42; A61F 13/74; A61F 13/84; A61F 2013/424; A61F 2013/425;
(Continued)

(56) References Cited

U.S. PATENT DOCUMENTS

| 3,460,123 A | 8/1969 | Bass |
| 3,508,235 A | 4/1970 | Baisden |

(Continued)

FOREIGN PATENT DOCUMENTS

| CN | 101196530 A | 6/2008 |
| CN | 106137156 A | 11/2016 |

(Continued)

OTHER PUBLICATIONS

Fish, Paul, et al., "Sensor technology: a smart way to manage continence", Australian Journal of Dementia Care, vol. 2 No. 1, Feb./Mar. 2013 pp. 35-37.

(Continued)

*Primary Examiner* — Catharine L Anderson
(74) *Attorney, Agent, or Firm* — Kimberly-Clark Worldwide, Inc.

(57) ABSTRACT

A garment configured for detecting leakage from an absorbent article underlying the garment and methods of detecting leakage from an absorbent article using such a garment are disclosed. The garment can include a substrate and a wetness detection system. The wetness detection system can include a first wetness detection mechanism disposed at a first detection zone on the substrate. The wetness detection system can further include a second wetness detection mechanism disposed at a second detection zone on the substrate. The second detection zone can be different than the first detection zone. In preferred embodiments, the first (Continued)

wetness detection mechanism and the second wetness detection mechanism can be configured to sense wetness electronically.

20 Claims, 5 Drawing Sheets

(58) Field of Classification Search
CPC ...... A61F 2013/8476; A61F 2013/8479; A61F 2013/8482
See application file for complete search history.

(56) References Cited

U.S. PATENT DOCUMENTS

| | | |
|---|---|---|
| 3,678,928 A | 7/1972 | Mozes |
| 3,778,570 A | 12/1973 | Shuman |
| 3,952,746 A | 4/1976 | Summers |
| 4,022,211 A | 5/1977 | Timmons et al. |
| 4,032,661 A | 6/1977 | Rowsell et al. |
| 4,068,221 A | 1/1978 | McClintock |
| 4,100,324 A | 7/1978 | Anderson et al. |
| 4,106,001 A | 8/1978 | Mahoney |
| 4,121,011 A | 10/1978 | Glover et al. |
| 4,136,163 A | 1/1979 | Watson et al. |
| 4,163,449 A | 8/1979 | Regal |
| 4,191,950 A | 3/1980 | Levin et al. |
| 4,192,311 A | 3/1980 | Felfoldi |
| 4,212,295 A | 7/1980 | Snyder |
| 4,230,688 A | 10/1980 | Rowsell et al. |
| 4,231,370 A | 11/1980 | Mroz et al. |
| 4,246,574 A | 1/1981 | Sanner |
| 4,252,845 A | 2/1981 | Griffiths et al. |
| 4,271,406 A | 6/1981 | Wilson |
| 4,347,503 A | 8/1982 | Uyehara |
| 4,356,479 A | 10/1982 | Wilson |
| 4,356,818 A | 11/1982 | Macias et al. |
| 4,459,425 A | 7/1984 | Amano et al. |
| 4,507,121 A | 3/1985 | Leung |
| 4,530,030 A | 7/1985 | Woest et al. |
| 4,539,559 A | 9/1985 | Kelly et al. |
| 4,571,750 A | 2/1986 | Barry |
| 4,610,678 A | 9/1986 | Weisman et al. |
| 4,642,250 A | 2/1987 | Spector |
| 4,653,491 A | 3/1987 | Okada et al. |
| 4,681,576 A | 7/1987 | Colon et al. |
| 4,704,108 A | 11/1987 | Okada et al. |
| 4,704,116 A | 11/1987 | Enloe |
| 4,705,513 A | 11/1987 | Sheldon et al. |
| 4,725,462 A | 2/1988 | Kimura |
| 4,738,260 A | 4/1988 | Brown |
| 4,744,113 A | 5/1988 | Kogut |
| 4,754,264 A | 6/1988 | Okada et al. |
| 4,768,023 A | 8/1988 | Xie |
| 4,796,014 A | 1/1989 | Chia |
| 4,800,370 A | 1/1989 | Vetecnik |
| 4,826,550 A | 5/1989 | Shimizu et al. |
| 4,834,733 A | 5/1989 | Huntoon et al. |
| 4,926,871 A | 5/1990 | Ganguly et al. |
| 4,940,464 A | 7/1990 | Van Gompel et al. |
| 4,977,906 A | 12/1990 | Di Scipio |
| 5,003,178 A | 3/1991 | Livesay |
| 5,036,859 A | 8/1991 | Brown |
| 5,043,704 A * | 8/1991 | Blakeney ............... A61F 13/42 340/573.5 |
| 5,060,638 A | 10/1991 | Bodine |
| 5,066,711 A | 11/1991 | Colon et al. |
| 5,114,781 A | 5/1992 | Morman |
| 5,116,662 A | 5/1992 | Morman |
| 5,121,630 A | 6/1992 | Calvin |
| 5,137,033 A | 8/1992 | Norton |
| 5,144,284 A | 9/1992 | Hammett |
| 5,150,002 A | 9/1992 | Van der Hoeck et al. |
| 5,151,092 A | 9/1992 | Buell et al. |
| 5,173,521 A | 12/1992 | Ishino |
| 5,174,656 A | 12/1992 | Dotan |
| 5,175,505 A | 12/1992 | Magenau et al. |
| 5,192,606 A | 3/1993 | Proxmire et al. |
| 5,197,958 A | 3/1993 | Howell |
| 5,221,228 A | 6/1993 | Pedroia |
| 5,224,769 A | 7/1993 | Holbrook et al. |
| 5,264,830 A | 11/1993 | Kline et al. |
| 5,266,592 A | 11/1993 | Grub et al. |
| 5,266,928 A | 11/1993 | Johnson |
| 5,284,703 A | 2/1994 | Everhart et al. |
| 5,291,181 A | 3/1994 | DePonte |
| 5,322,067 A | 6/1994 | Prater et al. |
| 5,341,127 A | 8/1994 | Smith |
| 5,341,673 A | 8/1994 | Burns et al. |
| 5,350,624 A | 9/1994 | Georger et al. |
| 5,354,289 A | 10/1994 | Mitchell et al. |
| H1376 H | 11/1994 | Osborn et al. |
| 5,384,411 A | 1/1995 | Robotti et al. |
| 5,389,093 A | 2/1995 | Howell |
| 5,392,032 A | 2/1995 | Kline et al. |
| 5,395,358 A | 3/1995 | Lu |
| 5,399,219 A | 3/1995 | Roessler et al. |
| 5,407,492 A | 4/1995 | Ohmi et al. |
| 5,416,469 A | 5/1995 | Colling |
| 5,454,376 A | 10/1995 | Stephens |
| 5,459,452 A | 10/1995 | DePonte |
| 5,469,145 A | 11/1995 | Johnson |
| 5,469,146 A | 11/1995 | Gurler |
| 5,475,835 A | 12/1995 | Hickey |
| 5,478,382 A | 12/1995 | Miller et al. |
| 5,486,166 A | 1/1996 | Bishop et al. |
| 5,486,227 A | 1/1996 | Kumar et al. |
| 5,490,846 A | 2/1996 | Ellis et al. |
| 5,537,095 A | 7/1996 | Dick et al. |
| 5,540,796 A | 7/1996 | Fries |
| 5,557,263 A | 9/1996 | Fisher et al. |
| 5,568,128 A | 10/1996 | Nair |
| 5,570,082 A | 10/1996 | Mahgerefteh et al. |
| 5,595,618 A | 1/1997 | Fries et al. |
| 5,617,488 A | 4/1997 | Hong et al. |
| 5,645,542 A | 7/1997 | Anjur et al. |
| 5,663,611 A | 9/1997 | Seats et al. |
| 5,702,377 A | 12/1997 | Collier et al. |
| 5,709,222 A | 1/1998 | Davallou |
| 5,713,881 A | 2/1998 | Rezai et al. |
| 5,722,968 A | 3/1998 | Datta et al. |
| 5,760,694 A | 6/1998 | Nissim et al. |
| 5,766,389 A | 6/1998 | Brandon et al. |
| 5,768,696 A | 6/1998 | Law |
| 5,780,896 A | 7/1998 | Ono |
| 5,790,035 A | 8/1998 | Ho |
| 5,790,036 A | 8/1998 | Fisher et al. |
| 5,796,345 A | 8/1998 | Leventis et al. |
| 5,802,611 A | 9/1998 | McKenzie et al. |
| 5,808,554 A | 9/1998 | Shuminov |
| 5,817,076 A | 10/1998 | Fard |
| 5,820,973 A | 10/1998 | Dodge et al. |
| 5,838,240 A | 11/1998 | Johnson |
| 5,844,862 A | 12/1998 | Cocatre-Zilgien |
| 5,845,644 A | 12/1998 | Hughes et al. |
| 5,868,723 A | 2/1999 | Al-Sabah |
| 5,881,731 A | 3/1999 | Remes |
| 5,883,028 A | 3/1999 | Morman et al. |
| 5,902,296 A | 5/1999 | Fluyeras |
| 5,903,222 A | 5/1999 | Kawarizadeh et al. |
| 5,904,671 A | 5/1999 | Navot et al. |
| 5,922,537 A | 7/1999 | Ewart et al. |
| 5,931,823 A | 8/1999 | Stokes et al. |
| 5,959,535 A | 9/1999 | Remsburg |
| 5,962,995 A | 10/1999 | Avnery |
| 5,964,743 A | 10/1999 | Abuto et al. |
| 6,060,638 A | 5/2000 | Paul et al. |
| 6,066,774 A | 5/2000 | Roe |
| 6,093,869 A | 7/2000 | Roe et al. |
| 6,097,297 A | 8/2000 | Fard |
| 6,101,366 A | 8/2000 | Castillo |
| 6,110,111 A | 8/2000 | Barnard |
| 6,135,945 A | 10/2000 | Sultan |
| 6,149,636 A | 11/2000 | Roe et al. |

(56) References Cited

U.S. PATENT DOCUMENTS

| | | | |
|---|---|---|---|
| 6,150,002 A | 11/2000 | Varona | |
| 6,160,198 A | 12/2000 | Roe et al. | |
| 6,163,262 A | 12/2000 | Wu | |
| 6,186,991 B1 | 2/2001 | Roe et al. | |
| 6,200,250 B1 | 3/2001 | Janszen | |
| 6,231,557 B1 | 5/2001 | Krautkramer et al. | |
| 6,246,330 B1 | 6/2001 | Nielsen | |
| 6,270,783 B1 | 8/2001 | Slavtcheff et al. | |
| 6,276,202 B1 | 8/2001 | Latarius | |
| 6,297,424 B1 | 10/2001 | Olson et al. | |
| 6,325,066 B1 * | 12/2001 | Hughes | A61F 5/48 |
| | | | 128/885 |
| 6,348,640 B1 | 2/2002 | Navot et al. | |
| 6,359,190 B1 | 3/2002 | Ter-Ovanesyan et al. | |
| 6,362,389 B1 | 3/2002 | McDowall et al. | |
| 6,372,951 B1 | 4/2002 | Ter-Ovanesyan et al. | |
| 6,373,263 B1 | 4/2002 | Netzer | |
| 6,373,395 B1 | 4/2002 | Kimsey | |
| 6,384,296 B1 | 5/2002 | Roe et al. | |
| 6,384,728 B1 | 5/2002 | Kanor et al. | |
| 6,392,542 B1 | 5/2002 | Stanley | |
| 6,407,492 B1 | 6/2002 | Avnery et al. | |
| 6,484,053 B2 | 11/2002 | Leelamanit et al. | |
| 6,486,227 B2 | 11/2002 | Nohr et al. | |
| 6,544,200 B1 | 4/2003 | Smith et al. | |
| 6,552,245 B1 | 4/2003 | Roessler et al. | |
| 6,559,772 B2 | 5/2003 | Zand et al. | |
| 6,562,297 B1 | 5/2003 | Bonstein et al. | |
| 6,580,013 B1 | 6/2003 | Belloso | |
| 6,583,722 B2 | 6/2003 | Jeutter et al. | |
| 6,603,403 B2 | 8/2003 | Jeutter et al. | |
| 6,617,488 B1 | 9/2003 | Springer et al. | |
| 6,627,233 B1 | 9/2003 | Wolf et al. | |
| 6,635,797 B2 | 10/2003 | Olson et al. | |
| 6,642,427 B2 | 11/2003 | Roe et al. | |
| 6,645,190 B1 | 11/2003 | Olson et al. | |
| 6,653,522 B1 | 11/2003 | Blumenthal et al. | |
| 6,663,611 B2 | 12/2003 | Blaney et al. | |
| 6,673,982 B1 | 1/2004 | Chen et al. | |
| 6,677,859 B1 | 1/2004 | Bensen | |
| 6,696,618 B2 | 2/2004 | Dodge, II et al. | |
| 6,710,221 B1 | 3/2004 | Pierce et al. | |
| 6,731,215 B2 | 5/2004 | Harms et al. | |
| 6,733,766 B2 | 5/2004 | Gott et al. | |
| 6,755,795 B2 | 6/2004 | Marmaropoulos et al. | |
| 6,756,521 B1 | 6/2004 | Breitkopf | |
| 6,772,454 B1 | 8/2004 | Barry et al. | |
| 6,772,708 B2 | 8/2004 | Klofta et al. | |
| 6,774,800 B2 | 8/2004 | Friedman et al. | |
| 6,780,896 B2 | 8/2004 | MacDonald et al. | |
| 6,870,479 B2 | 3/2005 | Gabriel | |
| 6,904,865 B2 | 6/2005 | Klofta et al. | |
| 6,929,819 B2 | 8/2005 | Underhill et al. | |
| 6,970,091 B2 | 11/2005 | Roe | |
| 7,002,054 B2 | 2/2006 | Allen et al. | |
| 7,049,969 B2 | 5/2006 | Tamai | |
| 7,141,715 B2 | 11/2006 | Shapira | |
| 7,159,532 B2 | 1/2007 | Klofta et al. | |
| 7,250,547 B1 | 7/2007 | Hofmeister et al. | |
| 7,306,764 B2 | 12/2007 | Mody | |
| 7,355,090 B2 | 4/2008 | Ales, III et al. | |
| 7,394,391 B2 | 7/2008 | Long | |
| 7,477,156 B2 | 1/2009 | Long et al. | |
| 7,489,252 B2 | 2/2009 | Long et al. | |
| 7,492,270 B2 | 2/2009 | Veerasamy | |
| 7,498,478 B2 | 3/2009 | Long et al. | |
| 7,642,396 B2 | 1/2010 | Ales, III et al. | |
| 7,649,125 B2 | 1/2010 | Ales, III et al. | |
| 7,731,665 B2 | 6/2010 | Lee et al. | |
| 7,812,731 B2 | 10/2010 | Bunza et al. | |
| 7,833,177 B2 | 11/2010 | Long et al. | |
| 7,977,529 B2 | 7/2011 | Bergman et al. | |
| 8,098,900 B2 | 1/2012 | Determan et al. | |
| 8,134,042 B2 | 3/2012 | Song et al. | |
| 8,222,476 B2 | 7/2012 | Song et al. | |
| 8,274,393 B2 | 9/2012 | Ales et al. | |
| 8,557,894 B2 | 10/2013 | Gil et al. | |
| 8,795,138 B1 | 8/2014 | Yeh et al. | |
| 8,866,624 B2 | 10/2014 | Ales, III et al. | |
| 9,138,354 B2 | 9/2015 | Nhan et al. | |
| 9,408,757 B2 | 8/2016 | Elfström et al. | |
| 10,111,590 B2 * | 10/2018 | Thoen | A61B 5/6891 |
| 10,350,115 B2 | 7/2019 | Long et al. | |
| 2001/0044588 A1 | 11/2001 | Mault | |
| 2002/0026164 A1 | 2/2002 | Camarero Roy et al. | |
| 2002/0145526 A1 | 10/2002 | Friedman et al. | |
| 2003/0028165 A1 | 2/2003 | Curro et al. | |
| 2003/0060789 A1 | 3/2003 | Shapira et al. | |
| 2003/0125682 A1 | 7/2003 | Olson et al. | |
| 2003/0171729 A1 | 9/2003 | Kaun et al. | |
| 2004/0089058 A1 | 5/2004 | De Haan et al. | |
| 2004/0102750 A1 | 5/2004 | Jameson | |
| 2004/0106202 A1 | 6/2004 | Zainiev et al. | |
| 2004/0111045 A1 | 6/2004 | Sullivan et al. | |
| 2004/0113801 A1 | 6/2004 | Gustafson et al. | |
| 2004/0118540 A1 | 6/2004 | Garnier et al. | |
| 2004/0131651 A1 | 7/2004 | Panero et al. | |
| 2004/0138546 A1 | 7/2004 | Reho et al. | |
| 2004/0138723 A1 | 7/2004 | Malick et al. | |
| 2004/0140897 A1 | 7/2004 | Fabre et al. | |
| 2004/0147888 A1 | 7/2004 | Huang et al. | |
| 2004/0172000 A1 | 9/2004 | Roe et al. | |
| 2004/0207530 A1 | 10/2004 | Nielsen | |
| 2004/0220538 A1 | 11/2004 | Panopoulos | |
| 2004/0236302 A1 | 11/2004 | Wilhelm et al. | |
| 2005/0033250 A1 * | 2/2005 | Collette | A61F 13/42 |
| | | | 604/361 |
| 2005/0046578 A1 | 3/2005 | Pires | |
| 2005/0054255 A1 | 3/2005 | Morman et al. | |
| 2005/0059941 A1 | 3/2005 | Baldwin et al. | |
| 2005/0120919 A1 | 6/2005 | Davies-Smith et al. | |
| 2005/0136772 A1 | 6/2005 | Chen et al. | |
| 2005/0137542 A1 | 6/2005 | Underhill et al. | |
| 2005/0156744 A1 | 7/2005 | Pires | |
| 2005/0195085 A1 | 9/2005 | Cretu-Petra | |
| 2005/0245839 A1 | 11/2005 | Stivoric et al. | |
| 2005/0251036 A1 | 11/2005 | Abuhamad | |
| 2005/0274470 A1 | 12/2005 | Shannon et al. | |
| 2005/0287356 A1 | 12/2005 | Li et al. | |
| 2006/0069360 A1 | 3/2006 | Long et al. | |
| 2006/0069362 A1 | 3/2006 | Odorzynski et al. | |
| 2006/0174693 A1 | 8/2006 | Chen et al. | |
| 2006/0229577 A1 | 10/2006 | Roe et al. | |
| 2006/0229578 A1 | 10/2006 | Roe et al. | |
| 2006/0258916 A1 | 11/2006 | Pietersen | |
| 2007/0017413 A1 | 1/2007 | Kwan et al. | |
| 2007/0048709 A1 | 3/2007 | Ales et al. | |
| 2007/0083174 A1 | 4/2007 | Ales et al. | |
| 2007/0089800 A1 * | 4/2007 | Sharma | D03D 15/0027 |
| | | | 139/388 |
| 2007/0142797 A1 | 6/2007 | Long et al. | |
| 2007/0142799 A1 | 6/2007 | Ales et al. | |
| 2007/0156106 A1 | 7/2007 | Klofta et al. | |
| 2007/0252712 A1 | 11/2007 | Allen et al. | |
| 2007/0270774 A1 | 11/2007 | Bergman et al. | |
| 2007/0273504 A1 | 11/2007 | Tran | |
| 2008/0021423 A1 | 1/2008 | Klofta et al. | |
| 2008/0041792 A1 | 2/2008 | Crnkovich et al. | |
| 2008/0048786 A1 | 2/2008 | Feldkamp et al. | |
| 2008/0054408 A1 | 3/2008 | Tippey et al. | |
| 2008/0058745 A1 | 3/2008 | Long et al. | |
| 2008/0076313 A1 | 3/2008 | Uitenbroek et al. | |
| 2008/0077040 A1 | 3/2008 | Ales et al. | |
| 2008/0077042 A1 | 3/2008 | Feldkamp et al. | |
| 2008/0082151 A1 | 4/2008 | Quincy et al. | |
| 2008/0129519 A1 | 6/2008 | Gabriel | |
| 2008/0132859 A1 | 6/2008 | Pires | |
| 2008/0145947 A1 | 6/2008 | Boga et al. | |
| 2008/0147030 A1 | 6/2008 | Nhan et al. | |
| 2008/0147031 A1 | 6/2008 | Long et al. | |
| 2008/0167535 A1 | 7/2008 | Stivoric et al. | |
| 2008/0168829 A1 * | 7/2008 | Paez | G01N 31/222 |
| | | | 73/73 |
| 2008/0243099 A1 | 10/2008 | Tippey et al. | |

(56) References Cited

U.S. PATENT DOCUMENTS

| | | |
|---|---|---|
| 2008/0262376 A1 | 10/2008 | Price |
| 2008/0266122 A1 | 10/2008 | Ales et al. |
| 2008/0278336 A1 | 11/2008 | Ortega et al. |
| 2008/0278337 A1 | 11/2008 | Huang et al. |
| 2008/0284608 A1 | 11/2008 | Long |
| 2008/0287747 A1 | 11/2008 | Mestrovic et al. |
| 2008/0306461 A1 | 12/2008 | Jan |
| 2009/0005748 A1 | 1/2009 | Ales et al. |
| 2009/0036012 A1 | 2/2009 | Nhan et al. |
| 2009/0036850 A1 | 2/2009 | Nhan et al. |
| 2009/0062756 A1 | 3/2009 | Long et al. |
| 2009/0062757 A1 | 3/2009 | Long et al. |
| 2009/0157024 A1 | 6/2009 | Song |
| 2009/0194532 A1 | 8/2009 | Yang et al. |
| 2009/0275908 A1 | 11/2009 | Song |
| 2009/0326417 A1 | 12/2009 | Ales, III et al. |
| 2010/0015658 A1 | 1/2010 | Yang et al. |
| 2010/0168694 A1 | 7/2010 | Gakhar et al. |
| 2010/0215542 A1 | 8/2010 | Hill et al. |
| 2010/0277324 A1 | 11/2010 | Yeh |
| 2011/0144602 A1 | 6/2011 | Long et al. |
| 2012/0053423 A1 | 3/2012 | Kenalty et al. |
| 2012/0157947 A1 | 6/2012 | Nhan et al. |
| 2012/0216607 A1 | 8/2012 | Sjöholm et al. |
| 2012/0268278 A1 | 10/2012 | Lewis et al. |
| 2012/0310190 A1* | 12/2012 | LaVon ................. A61F 13/625 604/361 |
| 2013/0018231 A1 | 1/2013 | Hong et al. |
| 2013/0110063 A1 | 5/2013 | Abraham et al. |
| 2013/0324955 A1 | 12/2013 | Wong et al. |
| 2014/0121473 A1 | 5/2014 | Banet et al. |
| 2014/0155850 A1 | 6/2014 | Shah et al. |
| 2014/0232516 A1 | 8/2014 | Stivoric et al. |
| 2014/0327546 A1 | 11/2014 | Carney et al. |
| 2015/0320609 A1 | 11/2015 | Thoen |
| 2016/0078176 A1 | 3/2016 | Ranta et al. |
| 2016/0120453 A1 | 5/2016 | Pop et al. |

FOREIGN PATENT DOCUMENTS

| | | |
|---|---|---|
| DE | 9309199 U1 | 10/1993 |
| DE | 19918681 A1 | 10/2000 |
| DE | 19937779 A1 | 2/2001 |
| DE | 19939902 A1 | 3/2001 |
| EP | 0446821 A2 | 9/1991 |
| EP | 0810847 B1 | 8/2000 |
| EP | 1424918 B1 | 11/2005 |
| GB | 2321990 A | 8/1998 |
| JP | 09033468 A | 2/1997 |
| JP | 09187431 A2 | 7/1997 |
| JP | 09220259 A | 8/1997 |
| JP | 09290001 A | 11/1997 |
| JP | 10314202 A | 12/1998 |
| JP | 2001318067 A | 11/2001 |
| JP | 2002071584 A | 3/2002 |
| JP | 2002153497 A | 5/2002 |
| JP | 2005013244 A | 1/2005 |
| JP | 2006043389 A | 2/2006 |
| JP | 2011022121 A | 2/2011 |
| KR | 100484478 B1 | 8/2005 |
| KR | 1020090081886 A | 7/2009 |
| KR | 1020160022183 A | 2/2016 |
| WO | 1991019471 A1 | 12/1991 |
| WO | 1995016425 A2 | 6/1995 |
| WO | 1999020216 A1 | 4/1999 |
| WO | 2000000082 A1 | 1/2000 |
| WO | 2000037009 A2 | 6/2000 |
| WO | 2000076443 A1 | 12/2000 |
| WO | 2001012150 A1 | 2/2001 |
| WO | 2001095845 A1 | 12/2001 |
| WO | 2003007997 A2 | 1/2003 |
| WO | 2003051254 A2 | 6/2003 |
| WO | 2004021944 A1 | 3/2004 |
| WO | 2004028429 A1 | 4/2004 |
| WO | 2004100763 A2 | 11/2004 |
| WO | 2005106465 A1 | 11/2005 |
| WO | 2006073096 A1 | 7/2006 |
| WO | 2007087674 A1 | 8/2007 |
| WO | 2010043368 A1 | 4/2010 |
| WO | 2010123425 A1 | 10/2010 |
| WO | 2016138331 A1 | 9/2016 |

OTHER PUBLICATIONS

Pogorelc, Deanna, "A diaper sensor and data is one startup's solution to helping manage incontinence in seniors", www.medcitynews.com/2012/08/a-diaper-sensor-and-data-is-one-startups-solution-to-helping-manage-incontinence-in-seniors/.

Yoon, Sung-Hoon and Xin-Sheng Chai, "Retention Rate Phenomena for Polyamide-Epichorohydrin Polymer in Papermaking Fibrous Colloidal Suspension," Journal of Industrial and Engineering Chemistry, vol. 13, No. 2, 2007, pp. 237-243.

* cited by examiner

GARMENT FOR DETECTING ABSORBENT ARTICLE LEAKAGE AND METHODS OF DETECTING ABSORBENT ARTICLE LEAKAGE UTILIZING THE SAME

BACKGROUND

Absorbent articles such as diapers, training pants, incontinence products, feminine hygiene products, swim undergarments, and the like, conventionally include a liquid permeable body-side liner, a liquid impermeable outer cover, and an absorbent structure. The absorbent structure is typically located between the outer cover and the liner for taking in and retaining liquids (e.g., urine) exuded by the wearer. The absorbent structure can be made of, for instance, superabsorbent particles. For a variety of potential reasons, some absorbent articles will leak urine or other body fluids. These potential reasons can include body position, movement, amount of urine and/or other exudates already in the product, body geometries of wearers, and other potential reasons. It is typically difficult to determine where, when, and how an absorbent article has leaked urine or other bodily fluids, especially when the absorbent article is being worn by a newborn or other very young wearers. In a similar fashion, it is equally difficult to predict how changes in designs of various features of absorbent articles may affect potential leakage considerations.

Various types of moisture or wetness indicators have been suggested for use in absorbent articles. The wetness indicators include various passive indicators such as indicator strips, printing, or other devices within each absorbent article. Wetness indicators can also include alarm devices that are designed to assist parents or attendants in identifying a wet absorbent article condition early on. Wetness-sensing bed pads are also available to indicate when urination has reached bedding. However, none of these indicators are designed to indicate leakage from the absorbent article itself and that can provide information as to the location and timing of the leakage. Additionally, sensors in bed mats can provide significant delay in detecting leakage, or may altogether not detect leakage of the absorbent article, due to additional layers that the body exudates must pass through between the absorbent article and the bed mat.

In view of the above, a need currently exists for a garment that includes a wetness detection system that can be used to determine when and where an absorbent article leaks.

SUMMARY

The present disclosure is generally directed to a garment configured for detecting leakage from an absorbent article underlying the garment. The garment can be configured to detect leakage of the absorbent article, a location of the leakage corresponding to the absorbent article, and the timing of the leakage, without having to visually inspect the absorbent article itself or modifying the construction of the absorbent article.

In one embodiment, a garment for detecting leakage from an absorbent article underlying the garment can include a substrate and a wetness detection system. The wetness detection system can include a first wetness detection mechanism disposed at a first detection zone on the substrate. The wetness detection system can also include a second wetness detection mechanism disposed at a second detection zone on the substrate. The second detection zone can be different than the first detection zone.

In another embodiment, a garment for detecting leakage from an absorbent article underlying the garment can include a substrate and a wetness detection system. The wetness detection system can include a first wetness detection mechanism disposed at a first detection zone on the substrate. The first detection zone on the substrate can correspond to a first location on the absorbent article selected from the group consisting of: a front end edge, a rear end edge, a first side edge, and a second side edge. The wetness detection system can further include a second wetness detection mechanism disposed at a second detection zone on the substrate. The second detection zone can be different than the first detection zone and can correspond to a second location on the absorbent article selected from the group consisting of: the front end edge, the rear end edge, the first side edge, and the second side edge. The wetness detection system can also include a controller in electrical communication with the first wetness detection mechanism and the second wetness detection mechanism. The first wetness detection mechanism and the second wetness detection mechanism can each be configured to detect wetness electronically.

In still another embodiment, a method for detecting leakage from an absorbent article can include providing an absorbent article on a test subject. The method can also include providing a garment including a wetness detection system. The wetness detection system can include a first wetness detection mechanism. The first wetness detection mechanism can be disposed on the substrate and can be configured to detect wetness being a result of leakage from the absorbent article. The wetness detection system can also include a controller in electrical communication with the first wetness detection mechanism. The controller can be configured to record activity of the first wetness detection mechanism. The method can further include applying the garment to the test subject such that the garment overlays the absorbent article on the test subject. The method can additionally include monitoring the wetness detection system to detect leakage from the absorbent article.

Other features and aspects of the present disclosure are discussed in greater detail herein.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
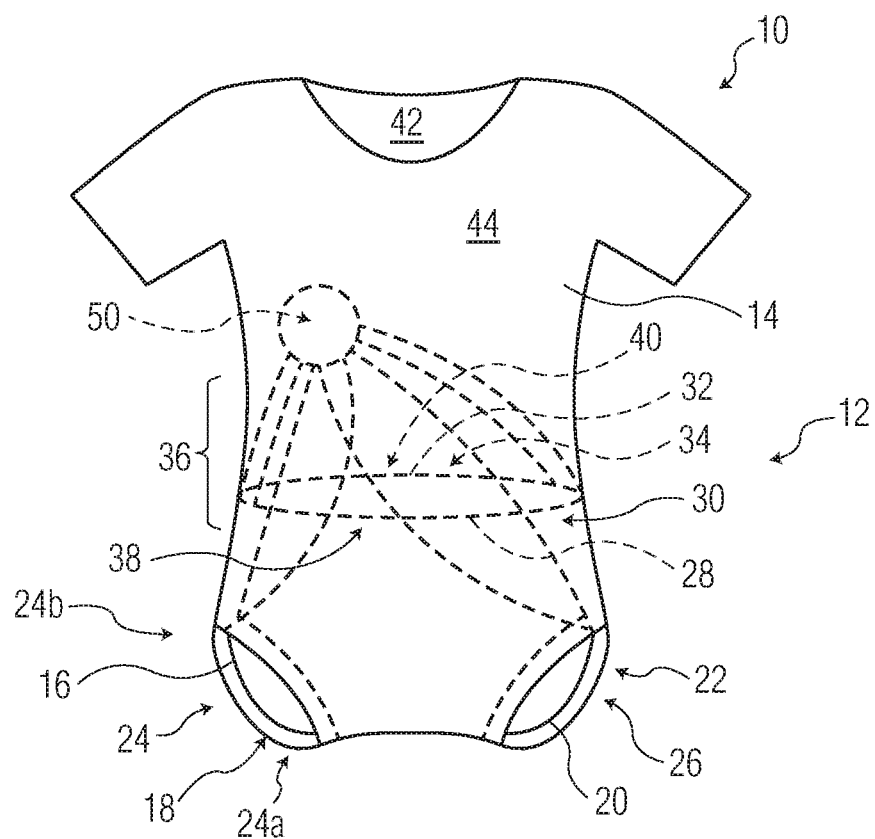
FIG. 1 is a front plan view of a first embodiment of a garment including a wetness detection system.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It is to be understood by one of ordinary skill in the art that the present discussion is a description of exemplary aspects only, and is not intended as limiting the broader aspects of the present disclosure.

The present disclosure is generally directed to a garment 10 including a wetness detection system 12 for determining when and where an absorbent article 100 underlying the garment 10 leaks a body exudate, and methods of utilizing the same. In accordance with the present disclosure, the garment 10 and wetness detection system 12 can have various configurations and designs.

For example, FIG. 1 illustrates an exemplary embodiment of a garment 10 including a wetness detection system 12. The garment can include a substrate 14 that forms at least a portion of the shape of the garment 10. In the embodiment illustrated in FIG. 1, the garment 10 can form an article of clothing known as a "onesie," typically worn by an infant or young child. However, it is contemplated that the garment 10 can form other articles of clothing, or portions thereof, worn by individuals of various ages, including, but not limited to, pants, shorts, undergarments, pajamas, gowns, etc. The garment 10 is configured such that an absorbent article 100 can be disposed under the garment 10, or in other words, underlying the garment 10. The substrate 14 can include various materials, however, it is preferable if the material can absorb wetness, as will be described further below.

The wetness detection system 12 can include various components. In some embodiments, the wetness detection system 12 can include one wetness detection mechanism 16, while in other embodiments, the wetness detection system 12 may include a plurality of wetness detection mechanisms 16, 20, 28, 32 such as the embodiment illustrated in FIG. 1.

The first wetness detection mechanism 16 can be disposed at a first detection zone 18 on the substrate 14. The wetness detection system 12 can also include a second wetness detection mechanism 20 disposed at a second detection zone 22 on the substrate 14. The first detection zone 18 can be different from the second detection zone 22. As illustrated in the embodiment of FIG. 1, the first wetness detection mechanism 16 and the second wetness detection mechanism 20 can be located near right and left leg openings 24, 26, respectively, of the garment 10. The wetness detection system 12 can also include a third wetness detection mechanism 28 disposed at a third detection zone 30 on the substrate 14 and a fourth wetness detection mechanism 32 disposed at a fourth detection zone 34 on the substrate 14. The third detection zone 30 can be different from the first detection zone 18 and the second detection zone 22. The fourth detection zone 34 can be different from the first detection zone 18, the second detection zone 22, and the third detection zone 30. As depicted in FIG. 1, the third wetness detection mechanism 28 and the fourth wetness detection mechanism 32 can be located near a central region 36 of the garment 10, such as where a wearer's waist may generally align. The third wetness detection mechanism 28 can be disposed on a front portion 38 of the garment 10, such as to generally align with a wearer's front waist. The fourth wetness detection mechanism 32 can be disposed on a rear portion 40 of the garment 10, such as to generally align with a wearer's rear waist. It is to be noted that the numbering of the wetness detection mechanisms 16, 20, 28, 32, as "first", "second", "third", etc. suggests no meaning other than to differentiate one wetness detection mechanism from another. As will be discussed in further detail below, the wetness detection mechanisms 16, 20, 28, 32 can be disposed in respective detection zones 18, 22, 30, 34 that generally correspond to specific locations on the absorbent article 100.

In some embodiments, such as the embodiment depicted in FIG. 1, the wetness detection mechanisms 16, 20, 28, 32 can be disposed on an internal surface 42 of the garment 10. However, it is contemplated that in other embodiments, the wetness detection mechanisms 16, 20, 28, 32 could be disposed on an external surface 44 of the garment 10.

The wetness detection mechanisms 16, 20, 28, 32 and their respective detection zones 18, 22, 30, 34 can be configured in a variety of ways. For example, the embodiment of FIG. 1 is configured such that the first and second wetness detection mechanisms 16, 18 are disposed on the substrate 14 at a first detection zone 18 and second detection zone 20, respectively, that are near the right leg opening 24 and left leg opening 26 of the garment 10. In an alternative embodiment, these two wetness detection mechanisms 16, 18 could be combined such that a single wetness detection mechanism provided a single detection zone at both the right leg opening 24 and the left leg opening 26 of the substrate 14. Similarly, the third wetness detection mechanism 28 disposed at a third detection zone 30 near the front portion 38 of the garment 10 and the fourth wetness detection mechanism 32 disposed at a fourth detection zone 34 near the rear portion 40 of the garment 10 could be combined such that a single wetness detection mechanism provided a single detection zone at both the front portion 38 and the rear portion 40 of the garment 10 in the central region 36 of the garment 10. As an example, it is contemplated that an alternative embodiment could include one wetness detection mechanism providing a detection zone disposed such that it is located near both leg openings 24, 26 of the garment 10 and another wetness detection mechanism providing another detection zone disposed such that it is located at both the front and rear portions 38, 40 of the garment 10 in the central region 36 of the garment.

Additionally, it is contemplated that the detection zones 18, 22, 30, 34 could be further subdivided than as shown in the embodiment illustrated in FIG. 1. As an example, it is contemplated that the first wetness detection mechanism 16 and the second wetness detection mechanism 20 could be disposed on the substrate 14 such that they are both located near the right leg opening 24 of the garment 10 to provide a first detection zone 18 near an inner portion 24a of the right leg opening 24 and a second detection zone 22 near an outer portion 24b of the right leg opening 24. It is contemplated that that the wetness detection mechanisms and respective detection zones could be even further subdivided. As an example, the garment 10 could be configured such that there are four wetness detection mechanisms disposed at four, separate detection zones all near the right leg opening 24 of the garment 16. It is contemplated that other wetness detection mechanisms and respective detection zones could be modified in a similar fashion.

The wetness detection mechanisms 16, 20, 28, 32 can be configured to detect wetness in a variety of fashions. In a preferred embodiment, the wetness detection mechanisms 16, 20, 28, 32 can be configured to detect wetness electronically. In other embodiments, the wetness detection mechanisms can be configured to detect wetness using capacitance (such as those described in U.S. Pat. No. 8,866,624), inductance (such as those described in U.S. Pat. No. 8,207,394), infra-red reflectance (U.S. patent Disclosure Ser. No. 12/636,888), each of which is incorporated herein by reference to the extent it does not conflict herewith, or any other suitable wetness detection technique known in the art. It is contemplated that one or more of the wetness detection mechanisms 16, 20, 28, 32 could all be configured to detect wetness utilizing the same technology (e.g., electronically), or could be configured such that at least two wetness detection mechanisms 16, 20, 28, 32 are configured to detect wetness utilizing different technologies (e.g., electronic and capacitance).

In embodiments where one or more wetness detection mechanisms 16, 20, 28, 32 are configured to detect wetness electronically, the one or more wetness detection mechanisms 16, 20, 28, 32 can include a conductive material. Exemplary conductive materials could include conductive threads, conductive tape, conductive rubber, or conductive wires such as copper. In a preferred embodiment, the wetness detection mechanisms 16, 20, 28, 32 can include conductive thread. An exemplary conductive thread that was used in embodiments and testing conducted herein was a silver coated thread that included 60 ohms/meter resistance. As an example, a conductive thread that could be used includes a Shieldex® 110/34 dtex 2 ply HC Premium Line that is a polyamide 6.6 filament yarn trilobal plated with 99% silver (model no. 400151011034PL), manufactured by Statex Produktions & Vertriebs GmbH. Of course, other suitable conductive threads or conductive materials could be selected for use in the wetness detection mechanisms 16, 20, 28, 32 as well. In a preferred embodiment that includes a wetness detection mechanism(s) 16, 20, 28, 32 that is configured to detect wetness electronically, the conductive materials can be monitored for changes in voltage across the conductive materials to determine if wetness has been detected.

Figure 1A:
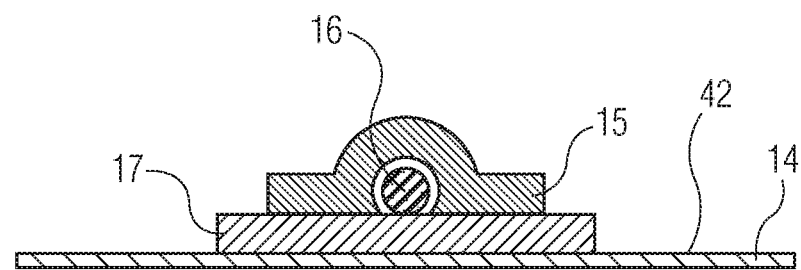
FIG. 1A is a cross-sectional view of a portion of an exemplary wetness detection mechanism of a garment and associated components.

In some embodiments, the wetness detection mechanisms 16, 20, 28, 32 can include associated components to aid in wetness detection. For example, FIG. 1A illustrates a cross-section of a wetness detection mechanism 16 coupled to a substrate 14. As depicted in FIG. 1A, the wetness detection mechanism 16 can be covered with a porous material 15 that is configured to prevent skin contact on a test subject 120, but that would not disrupt fluid from a leak from reaching the wetness detection mechanism 16. Additionally or alternative, in some embodiments, the substrate 14 could include a water-resistant or water-proof backing 17 coupled to the substrate 14 in the areas of the wetness detection mechanism 16 to aid in trapping liquid from a leak in the absorbent article 100 from leaving the garment 10 near the wetness detection mechanism 16. As shown in FIG. 1A, the water-resistant or water-proof backing 17 could be disposed between the internal surface 42 of the substrate 14 and the wetness detection mechanism 16. It is also contemplated that the water-resistant or water-proof backing 17 could be disposed on the external surface 44 of the garment 10 in the area of the wetness detection mechanism 16 to aid in trapping liquid from a leak in the absorbent article 100 from leaving the garment 10 near the wetness detection mechanism 16. Although only depicted for one exemplary wetness detection mechanism 16, this configuration of utilizing a porous material 15 and/or a water-resistant or water-proof backing 17 can be utilized with additional wetness detection mechanisms 20, 28, 32 in the garment 10, if desired.

The wetness detection system 12 can also include a controller 50. The controller 50 can be in electrical communication with the wetness detection mechanisms 16, 20, 28, 32. For example, in the embodiment illustrated in FIG. 2, the wetness detection mechanisms 16, 20, 28, 32 are wired to inputs and outputs (not labeled) of the controller 50. In embodiments where one or more wetness detection mechanisms 16, 20, 28, 32 are configured to detect wetness electronically, the controller 50 can supply voltage to the conductive material(s) (e.g., conductive threads) that form at least part of the wetness detection mechanism(s) 16, 20, 28, 32 and monitor for a change in voltage across such conductive material(s). The controller 50 can be configured to record activity of the wetness detection mechanisms 16, 20, 28, 32 over time. In one example, a controller 50 can be a microcontroller, such as the LilyPad Arduino USB board manufactured by Arduino. The controller 50 can include a power source (not labeled), such as a rechargeable battery. The controller 50 can include variety of input and output connections. As will be described further below, the controller 50 can be in electrical communication with a computer 60 (such as illustrated in FIG. 3). The controller 50 can be in electrical communication with a computer 60 via a wired connection 62 (e.g., USB connection) as illustrated in FIG. 3, or via a wireless connection (e.g., Bluetooth).

Figure 2:
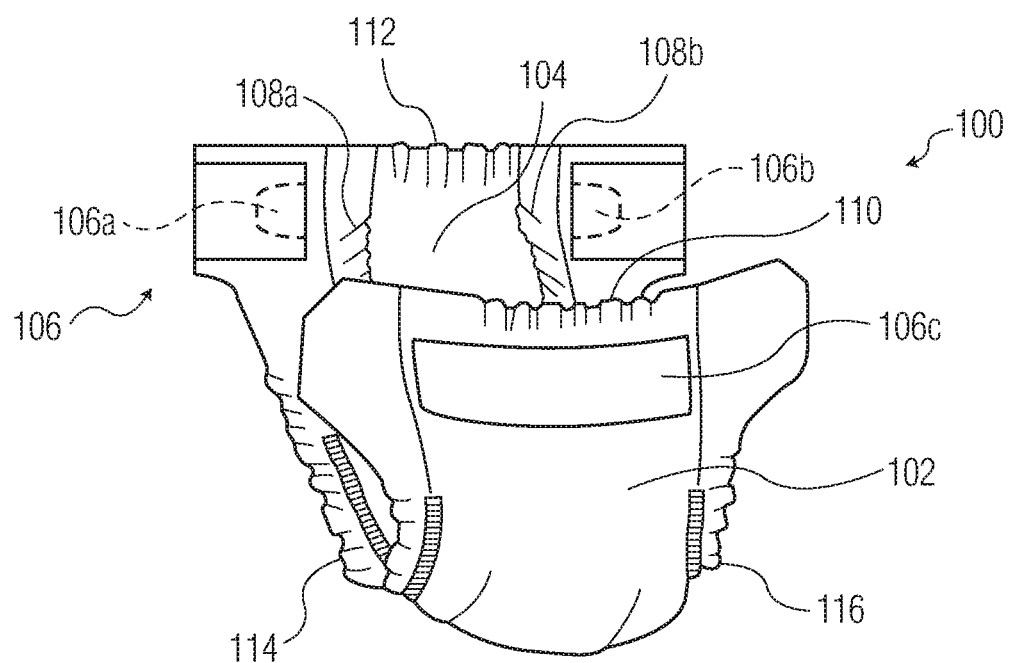
FIG. 2 is a perspective view of an exemplary absorbent article.
Figure 3:
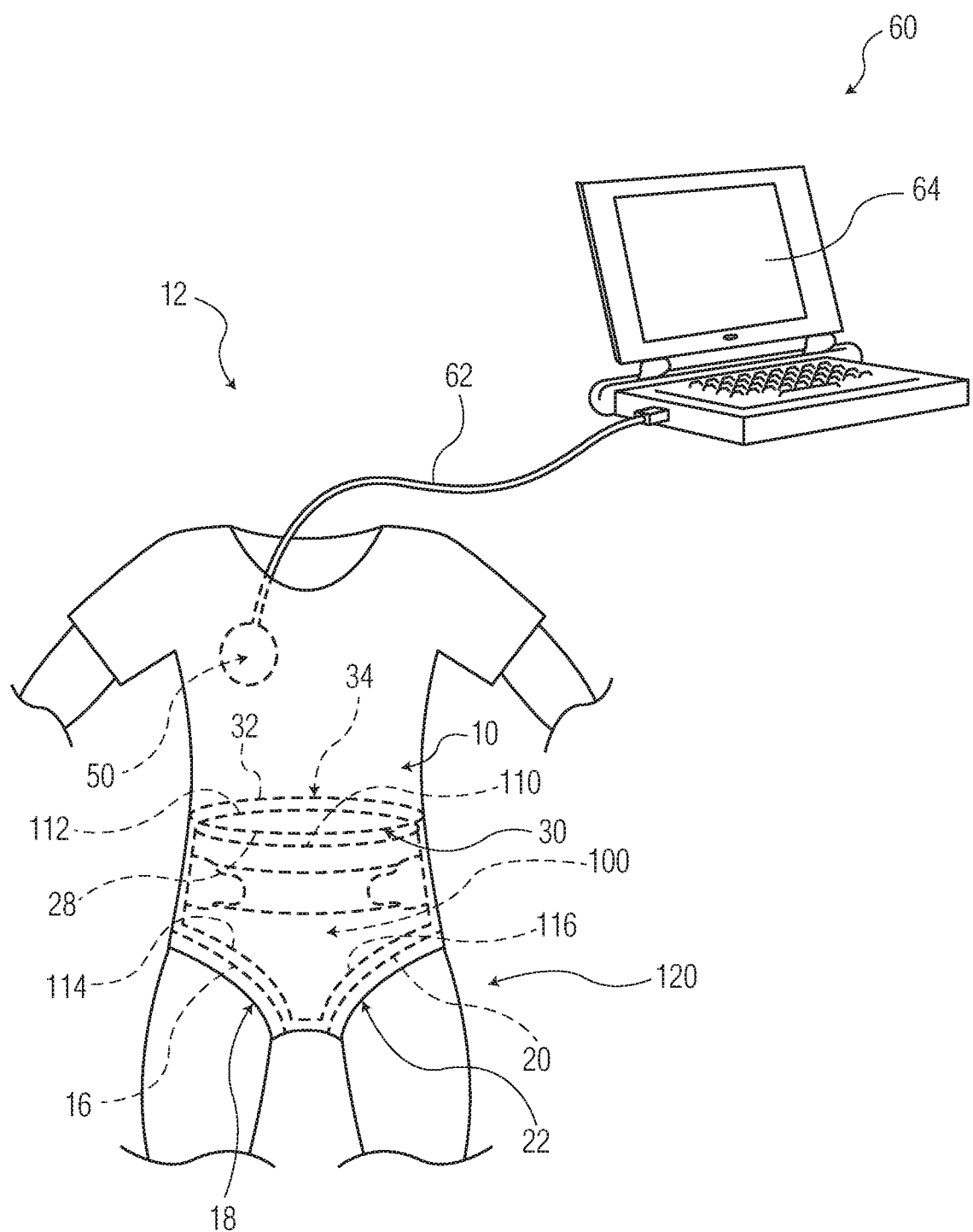
FIG. 3 is a perspective view of the garment of the embodiment of FIG. 1 overlaying an absorbent article on a test subject, the garment being in electrical communication with a computer.

As illustrated in FIG. 2, an exemplary absorbent article 100, in the form of a diaper, is illustrated. The absorbent article 100 can be disposable or not. It is understood that the present disclosure is suitable for use with various other absorbent articles intended for personal wear, including but not limited to diaper pants, training pants, swim pants, feminine hygiene products, incontinence products, medical garments, surgical pads and bandages, other personal care or health care garments, and the like, without departing from the scope of the present disclosure.

By way of illustration only, various materials and methods for constructing absorbent articles such as the absorbent article 100 of the various aspects of the present disclosure are disclosed in PCT Patent Disclosure WO 00/037009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

The absorbent article 100 can include an outer cover 102 and a bodyside liner 104. The absorbent article 100 can also include a fastening system 106, which in some embodiments, can include a pair of rear fasteners 106a, 106b and a front fastener 106c. The rear fasteners 106a, 106b can be a hook type fastener, and the front fastener 106c can be a loop type fastener. Of course, it is contemplated that other types of fastening systems 106 can be used, or completely omitted, and still be within the scope of this disclosure. The absorbent article 100 can also include a pair of leg flaps 108a, 108b. The absorbent article 100 can also include an absorbent core (not labeled) between the bodyside liner 104 and the outer cover 102.

As illustrated in FIG. 2, the absorbent article 100 can include a front end edge 110 and a rear end edge 112. The front end edge 110 can be opposite from the rear end edge 112. The front end edge 110 can be configured to be near a test subject's front waist region when the absorbent article 100 is placed on a test subject 120, such as illustrated in FIG. 3. Similarly, the rear end edge 112 can be configured to be near a test subject's rear waist region when the absorbent article 100 is placed on a test subject 120. The absorbent article 100 can also include a first side edge 114 and a second side edge 116. The first side edge 114 and the second side edge 116 can extend from the front end edge 110 to the rear end edge 112. In embodiments where the absorbent article 100 is in the form of a diaper, diaper pant, training pant, swim pant, or an incontinent product, the first side edge 114 and the second side edge 116 can form leg openings for the test subject 120 when the absorbent article 100 is placed on the test subject, such as illustrated in FIG. 3.

As depicted in FIG. 3, the garment 10 can be utilized to detect leakage from an absorbent article 100 that is placed on a test subject 120. FIG. 3 depicts the garment 10 and absorbent article 100 described above and illustrated in FIGS. 1 and 2, respectively, however, the connective portions of the wetness detection mechanisms 16, 20, 28, 32 to the controller 50 are not shown in FIG. 3 for clarity purposes.

In some aspects of the disclosure, the test subject 120 can be a mannequin that can be operated to remain motionless (i.e., static), or can have capability to move during testing (i.e., dynamic). Such a test subject 120 can be positioned in a variety of configurations to mimic body positions that a potential user of the absorbent article 100 could be in when wearing such an absorbent article 100. For example, the test subject 120 could be configured to be in a standing up-right position, a sitting position, or laying on its side, back, or front. As noted above, the test subject 120, when in mannequin form, can be manipulated to move to simulate body movements, including, but not limited to, crawling, walking, running, or moving from a sitting to a standing position, or vice versa. Such a test subject 120 that is a mannequin may be utilized in a laboratory environment under controlled conditions for design and/or development purposes of an absorbent article 100. In some embodiments, the test subject 120 could be a mannequin that is meant to remain stationary while the absorbent article 100 is insulted with a simulated body exudate insult until leakage is detected.

Alternatively, the test subject 120 could be an actual person that is wearing the absorbent article 100. Using the garment 10 on a test subject 120 that is an actual person could be in a testing facility for gathering data on the absorbent article 100 for design and/or development purposes of the absorbent article 100, or to be used to determine if an absorbent article 100 needs to be changed by a caregiver because fluid from the absorbent article 100 has begun to leak onto the surrounding garment 10. Such a use can provide an advantage over prior systems that utilized bed mats with electronic wetness sensing that may have had a delayed finding of leakage due to clothing and bedding absorbing the leaked fluid before the bed mat. Additionally, some bed mats utilizing sensing can be subject to false alarms of leaks from an individual drooling.

Referring still to FIG. 3, the wetness detection system 12 can be configured such that one or more of the wetness detection mechanisms 16, 20, 28, 32 provide a detection zone 18, 22, 30, 34 that corresponds to one or more particular locations of the absorbent article 100. More specifically, the detection zones 18, 22, 30, 34 provided by wetness detection mechanisms 16, 20, 28, 32 can correspond to particular locations of the absorbent article 100 that are of interest to be monitored for leakage from the absorbent article 100. For example, in the exemplary embodiment of FIG. 3, the garment 10 includes a wetness detection system 12 that is configured such that the first wetness detection mechanism 16 provides a first detection zone 18 that corresponds to the first side edge 114 of the absorbent article 100. The second wetness detection mechanism 20 provides a second detection zone 22 that corresponds to the second side edge 116 of the absorbent article 100. Additionally, the third wetness detection mechanism 28 provides a third detection zone 30 that corresponds to the front end edge 110 of the absorbent article 100 and the fourth wetness detection mechanism 32 provides a fourth detection zone 34 that corresponds to the rear end edge 112 of the absorbent article 100.

As previously discussed, it is contemplated that the wetness detection system 12 of the garment 10 can be configured in a variety of ways to assist in detecting the position in which leakage occurs from an absorbent article 100. In one alternative embodiment, the wetness detection system 12 can be configured such that the first wetness detection mechanism 16 would provide a first detection zone 18 that corresponds to both the first side edge 114 and the second side edge 116 of the absorbent article 100. Such a configuration could utilize a single wetness detection mechanism 16 to monitor whether a leak occurred from the absorbent article 100 near the first side edge 114 or the second side edge 116 of the absorbent article 100. In such an embodiment, a single wetness detection mechanism 16 can provide a first detection zone 18 that corresponds to more than one location of the absorbent article 100 that may be of interest to monitor for leaks from the absorbent article 100. Of course, the wetness detection system 12 could potentially include one or more wetness detection mechanisms providing detection zones corresponding to other locations of the absorbent article as well. Benefits of this type of configuration include simplified construction of the garment 10 and wetness detection system 12 and reduced cost.

In another contemplated configuration, the wetness detection system 12 of the garment 10 can be configured such that multiple wetness detection mechanisms 16, 20, 28, 32 provide detection zones 18, 22, 30, 34 corresponding to a single location on the absorbent article 100 that may be of interest to monitor for leaks from the absorbent article 100. As an example, it may be desirable to have four wetness detection mechanisms 16, 20, 28, 32 provide four detection zones 18, 22, 30, 34 all corresponding to a first side edge 114 of the absorbent article 100. In such a configuration, the detection zones 18, 22, 30, 34 could be configured to correspond to specific locations along the first side edge 114 in relation to its position on the test subject 120, such as, (a) right leg opening, top position; (b) right leg opening, bottom position; (c) right leg opening, front position; and (d) right leg opening, rear position. This exemplary configuration could provide the wetness detection system 12 with the advantage of a higher degree of specificity as to the location of a leak from the absorbent article 100, which can be useful in the design and development of an absorbent article 100. Of course, the wetness detection system 12 could potentially include one or more wetness detection mechanisms providing detection zones corresponding to other locations of the absorbent article 100 as well.

As can be seen from above, the wetness detection system 12 of the garment 10 can be configured in a variety of ways. Importantly, the wetness detection system 12 of the garment 10 can be customizable to the particular testing that is to be completed or the data that would be helpful in understanding locations on the absorbent article 100 that may leak or that actually have leaked. Some embodiments of the garment 10 may be configured such that one or more wetness detection mechanisms provide higher specificity as to the location of a leak from the absorbent article 100, while one or more wetness detection mechanisms provide more generalized feedback as to the location of a leak from the absorbent article 100. As an example, the garment 10 could be configured such that one wetness detection mechanism provides a detection zone corresponding to only a portion of the first side edge 114 of the absorbent article 100 (e.g., right leg opening, top position), whereas another wetness detection mechanism can provide a detection zone that corresponds to both the front end edge 110 and the rear end edge 112 of the absorbent article 100 that define an entire waist opening for the absorbent article 100. In other words, it is contemplated that a garment 10 can be configured such that the wetness detection system 12 includes at least two wetness detection mechanisms that are configured differently from one another, such as by having differing levels of specificity as to the location of a leak.

As discussed above, the garment 10 can overlay an absorbent article 100 and the wetness detection system 12 of the garment 10 can monitor for leakage of the absorbent article 100 when on a test subject 120 in a variety of conditions of the test subject 120. If the test subject 120 is a mannequin, the test subject 120 can be configured to insult the absorbent article 100 to replicate a potential user excreting a body exudate into the absorbent article 100, such as urine, feces, menses, or other body exudate. For example, saline solution can be utilized to replicate an insult of urine into the absorbent article 100. After such a test condition, the wetness detection system 12 on the garment 10 can monitor the absorbent article 10 for leakage. In some embodiments, the controller 50 of the wetness detection system 12 can record and/or transmit data of the one or more wetness detection mechanisms 16, 20, 28, 32 over time. In some embodiments, the data can be stored and then later be analyzed to determine whether a leak(s) occurred from the absorbent article 100 and when such leak(s) occurred from the absorbent article 100. Depending on the level of specificity to which the wetness detection mechanisms 16, 20, 28, 32 are configured on the wetness detection system 12, the data can additionally be analyzed to determine where such leak(s) occurred from the absorbent article 100. As discussed above, the level of detail can be as general or as specific as to the particular location of the leak(s) with respect to the absorbent article 100 depending on the amount and placement of the wetness detection mechanism(s) to provide the desired detection zones. As discussed above, configuring the wetness detection system 12 to have more wetness detection mechanisms can provide detection zones that are smaller in size, and thus, provide more specificity for monitoring the location(s) of a leak(s) from the absorbent article 100.

As illustrated in FIG. 3, in some embodiments, the wetness detection system 12 can be additionally include a computer 60 that is in electrical communication with the controller 50. The computer 60 can be a commonly-available personal computer or laptop. In some embodiments, the computer 60 can be in electrical communication with the controller 50 via a wired connection 62 (e.g., a USB connection). Alternatively, the computer 60 can be in electrical communication with the controller 50 via a wireless connection (e.g., Bluetooth connection). The computer 60 can include memory for storing data generated during testing, such as recorded data from the wetness detection system 12. The computer 60 can also be configured to interpret data from the wetness detection system 12, such as the timing and location that a leak is sensed on the garment 10 from the absorbent article 100. In some embodiments, the computer 60 can be configured to provide a notification message or alarm (in various forms) of such leakage information. Exemplary signals could include an audible signal, a tactile signal, an electromagnetic signal, a wireless signal, a visual signal, any other suitable signal, or any combination of these.

In some embodiments, the computer 60 can also be in electrical communication with the test subject 120 and/or other test equipment for operating various testing situations such as controlling when an insult to the absorbent article 100 occurs and how and when the test subject 120 will move during testing. The computer 60 can include features such as an output interface 64. The output interface 64 can display the activity of the wetness detection system 12 over time.

By having a wetness detection system 12 that can record the activity of the one or more wetness detection mechanisms over time, the wetness detection system 12 can provide the advantage within a testing environment of not requiring an individual to be present to watch the test being conducted to visually look for leak(s) from the absorbent article 100 and to record such information. In some past systems, one would need to watch the test being conducted for visual signs of leakage from the absorbent article 100 and then examine the absorbent article (such as by reviewing wetness indicia printed on the absorbent article) and/or examine an overlying garment to try to determine the location of the leak from the absorbent article 100. The garments 10 including a wetness detection system 12 as described herein can provide more accurate information as to the location of a leak(s) from the absorbent article and the time that such leak(s) occurred, with less intervention with the testing process. This benefit can apply whether the test subject 120 is a mannequin or an actual person wearing the absorbent article 100. Additionally, this benefit can be realized whether the data is documented and recorded on the controller 50 and then later analyzed, or if the data is communicated directly to a computer 60 (either via a wired or wireless connection) and monitored during the test conditions.

As discussed above, garments 10 described herein provide several benefits for testing purposes. Understanding the risks of leakage can be very important to the manufacturer of absorbent articles, and the results of such understanding can be very important to an absorbent article user and/or caregivers. Components of this understanding include body position of a test subject, when urination occurs, whether a leak occurs upon urination, where and when in the absorbent article 100 a leak emerges, in which body positions the absorbent article 100 does not leak, and in which body positions the absorbent article 100 does leak, and the capacity and/or rate of an insult prior causing leakage in an absorbent article 100. This provides valuable input to a manufacturer to help determine how to design absorbent articles to minimize leakage.

Additionally, garments 10 as described herein could provide benefits for alerting caregivers more timely as to when an absorbent article 100 has reached full capacity and needs to be changed.

Exemplary Tests of Garments

Figure 4:
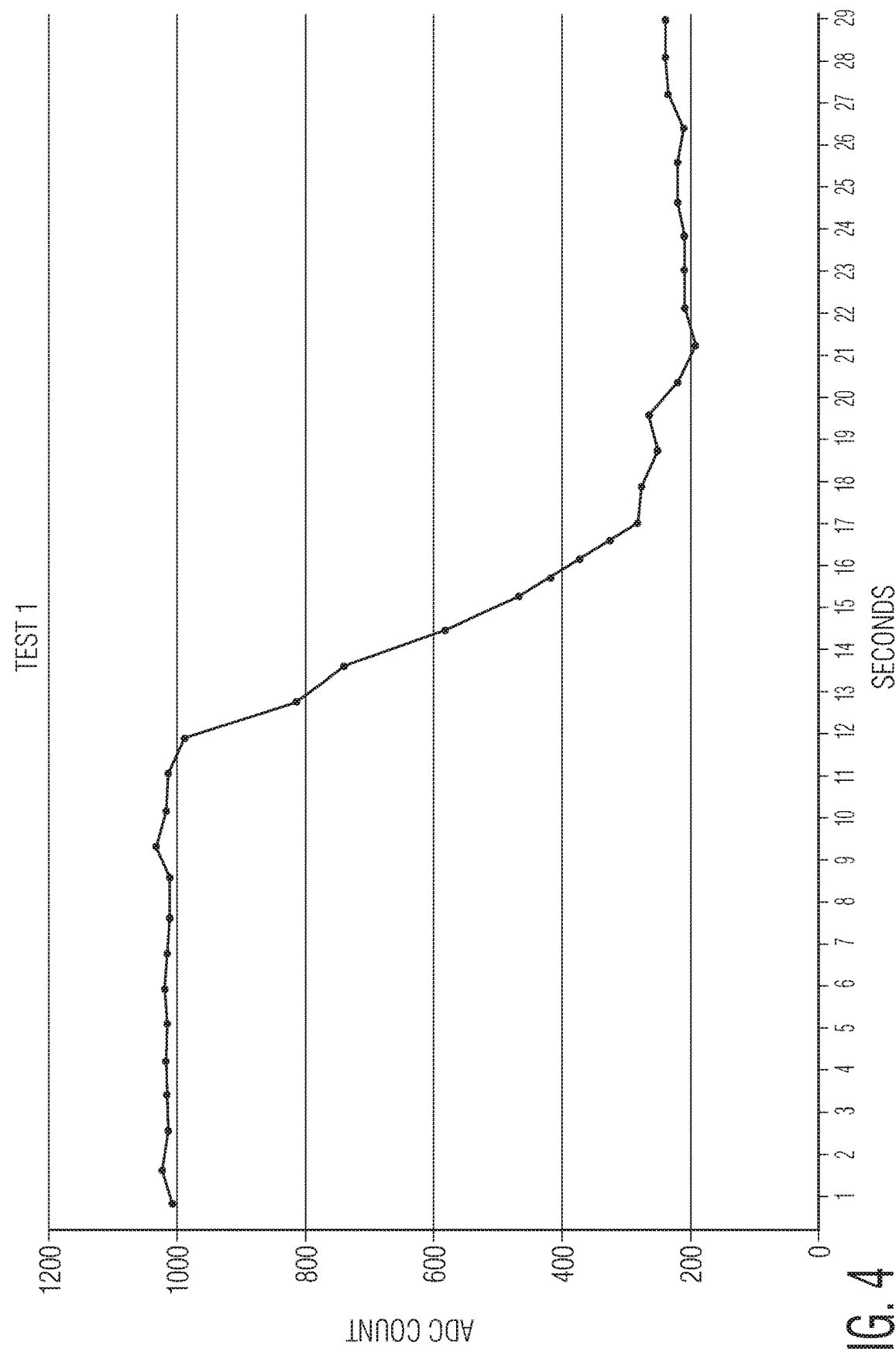
FIG. 4 is a graphical illustration depicting the output of a garment including a wetness detection system showing the Analog to Digital Converter (ADC) Count over time in a first test.
Figure 5:
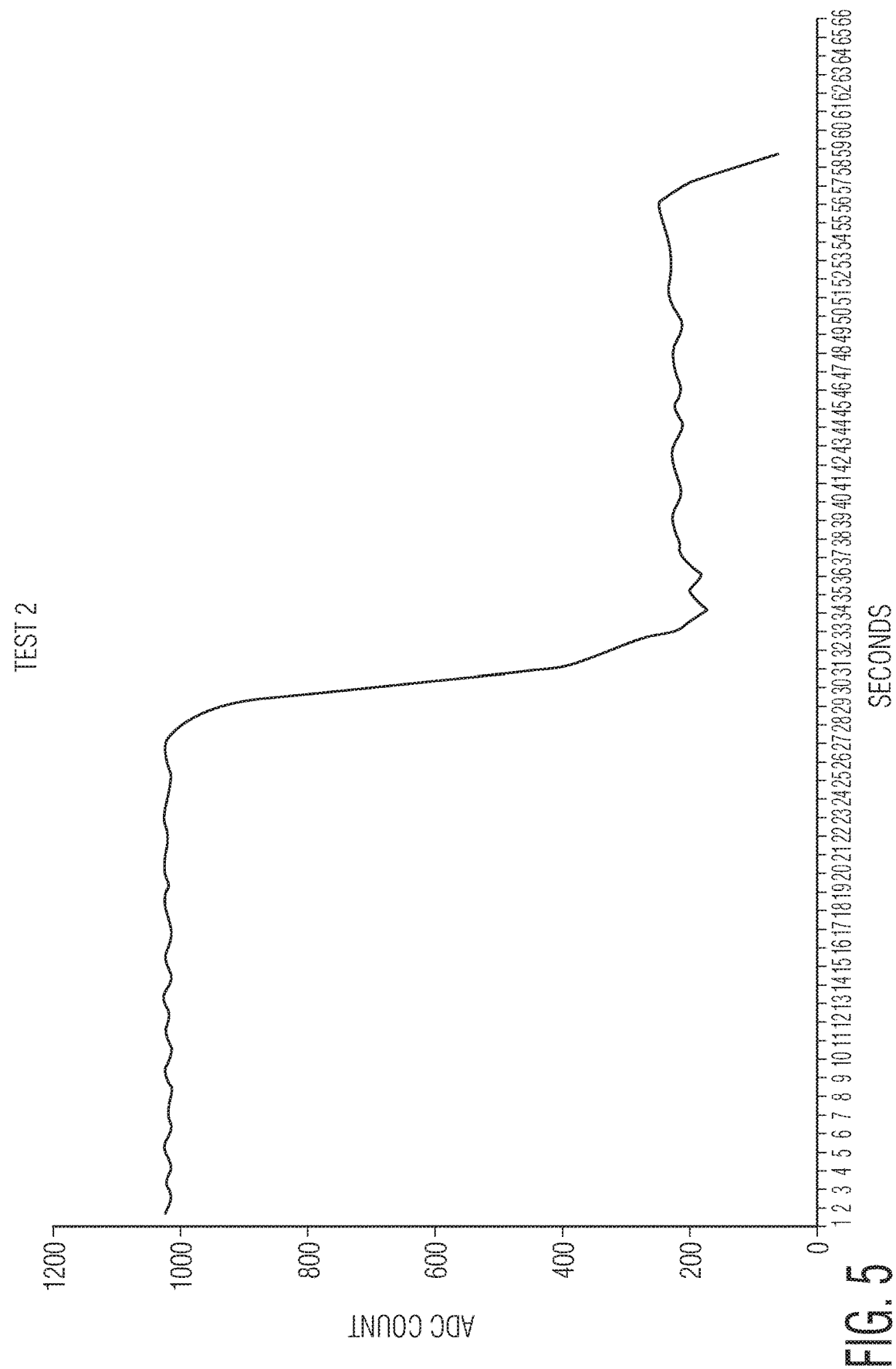
FIG. 5 is a graphical illustration depicting the output of a garment including a wetness detection system showing the ADC Count over time in a second test.

FIGS. 4 and 5 illustrate exemplary data outputs from a computer 60 that was connected to a wetness detection system 12 (including a controller 50) that monitored two tests (Test 1, Test 2), by recording and displaying activity of a wetness detection mechanism over time. For Test 1 and Test 2 that are illustrated in FIGS. 4 and 5, the wetness detection mechanism was a silver coated conductive thread that included 60 ohms/meter resistance and the conductive threads were taped to the substrate 14 forming the garment 10. The conductive threads were connected to a controller 50. The controller 50 for each of Test 1 and Test 2 was a LilyPad Arduino USB board 1DE 1.6.9, manufactured by Arduino. The controller 50 applied 3.3 VDC to the threads and the controller 50 monitors the voltage across the threads. A dry condition can result in approximately the full 3.3 VDC appearing across the threads, whereas a wet condition can result in significantly reduced voltage across the threads. In each test, 2 mL of saline solution were released on top of the conductive threads forming the wetness detection mechanism to simulate a leak from an absorbent article onto the test garment 10.

For Test 1 illustrated in FIG. 4, the garment 10 was a 60% polyester/40% cotton onesie manufactured by Mini Bean. In Test 1, the Analog to Digital Converter (ADC) Count was monitored over time. The ADC Count correlates to the voltage across the conductive threads and had a full scale of 1024 counts, such that each count is equal to approximately 0.003223V (3.3V/1024 counts). As depicted in FIG. 4, the test began with the ADC Count remaining substantially constant around a value of 1000 counts (approximately 3.2V) until the simulated insult begins to wet the wetness detection mechanism at approximately 14 seconds into the test, at which time the ADC Count is significantly reduced. The ADC Count then stabilizes to approximately 200 counts (approximately 0.64V) after the wetness detection mechanism is fully wetted.

In FIG. 5, Test 2 was conducted where the garment 10 a 100% polyester footed-pajamas manufactured by Carter's, Inc. The ADC Count was monitored over time and the test began with the ADC Count remaining substantially constant around a value of 1000 counts (approximately 3.2V) until the simulated insult begins to wet the wetness detection mechanism at approximately 26 seconds into the test, at which time the ADC Count is significantly reduced. The ADC Count then stabilizes to approximately 200 counts (approximately 0.64V) after the wetness detection mechanism is fully wetted. In Test 2, a further reduction in the ADC count occurred at approximately 56 seconds into the test, when it is believed that the conductive wires of the wetness detection mechanism shorted out.

EMBODIMENTS

Embodiment 1

A garment configured for detecting leakage from an absorbent article underlying the garment, the garment comprising: a substrate; and a wetness detection system, the wetness detection system comprising: a first wetness detection mechanism disposed at a first detection zone on the substrate; and a second wetness detection mechanism disposed at a second detection zone on the substrate, the second detection zone being different than the first detection zone.

Embodiment 2

The garment of embodiment 1, wherein the wetness detection system further comprises: a controller in electrical communication with the first wetness detection mechanism and the second wetness detection mechanism.

Embodiment 3

The garment of embodiment 1 or 2, wherein the first wetness detection mechanism and the second wetness detection mechanism are each configured to detect wetness electronically.

Embodiment 4

The garment of embodiment 3, wherein the first wetness detection mechanism and the second wetness detection mechanism each comprise conductive thread.

Embodiment 5

The garment of any one of the preceding embodiments, wherein the first detection zone on the substrate corresponds to a first location on the absorbent article selected from the group consisting of: a front end edge, a rear end edge, a first side edge, and a second side edge.

Embodiment 6

The garment of embodiment 5, wherein the second detection zone on the substrate corresponds to a second location on the absorbent article selected from the group consisting of: the front end edge, the rear end edge, the first side edge, and the second side edge.

Embodiment 7

The garment of embodiment 6, wherein the wetness detection system further comprises a third wetness detection mechanism disposed at a third detection zone on the substrate, the third detection zone on the substrate being different than the first detection zone and the second detection zone on the substrate, the third detection zone on the substrate corresponding to a third location on the absorbent article selected from the group consisting of: the front end edge, the rear end edge, the first side edge, and the second side edge.

Embodiment 8

The garment of embodiment 2, wherein the wetness detection system further comprises a power source.

Embodiment 9

The garment of embodiment 2 or embodiment 8, wherein the controller is configured to be in electrical communication with a computer.

Embodiment 10

A garment configured for detecting leakage from an absorbent article underlying the garment, the garment comprising: a substrate; and a wetness detection system, the wetness detection system comprising: a first wetness detection mechanism disposed at a first detection zone on the substrate, the first detection zone on the substrate corresponds to a first location on the absorbent article selected from the group consisting of: a front end edge, a rear end edge, a first side edge, and a second side edge; a second wetness detection mechanism disposed at a second detection zone on the substrate, the second detection zone being different than the first detection zone and corresponding to a second location on the absorbent article selected from the group consisting of: the front end edge, the rear end edge, the first side edge, and the second side edge; and a controller in electrical communication with the first wetness detection mechanism and the second wetness detection mechanism, the first wetness detection mechanism and the second wetness detection mechanism each being configured to detect wetness electronically.

Embodiment 11

The garment of embodiment 10, wherein the wetness detection system further comprises: a third wetness detection mechanism disposed at a third detection zone on the substrate, the third detection zone being different than the first detection zone and the second detection zone and corresponding to a third location on the absorbent article selected from the group consisting of: the front end edge, the rear end edge, the first side edge, and the second side edge; and wherein the third wetness detection mechanism is configured to detect wetness electronically.

Embodiment 12

The garment of embodiment 10 or embodiment 11, wherein the wetness detection system further comprises a power source.

Embodiment 13

The garment of any one of embodiments 10-12, wherein the controller is configured to be in electrical communication with a computer, the computer being configured to monitor the activity of the first wetness detection mechanism and the second wetness detection mechanism over time.

Embodiment 14

A method of detecting leakage from an absorbent article, the method comprising: providing an absorbent article on a test subject; providing a garment including a wetness detection system, the wetness detection system comprising: a first wetness detection mechanism, the first wetness detection mechanism disposed on the substrate and being configured to detect wetness being a result of leakage from the absorbent article; and a controller in electrical communication with the first wetness detection mechanism, the controller configured to record activity of the first wetness detection mechanism; applying the garment to the test subject such that the garment overlays the absorbent article on the test subject; and monitoring the wetness detection system to detect leakage from the absorbent article.

Embodiment 15

The method of embodiment 14, wherein the wetness detection system further comprises a computer in electrical communication the controller, the computer including an output interface for monitoring the wetness detection system to detect leakage from the absorbent article.

Embodiment 16

The method of embodiment 15, wherein the computer is configured to record a location of leakage of the absorbent article and a time of leakage of the absorbent article based on monitoring the activity of the wetness detection system.

Embodiment 17

The method of any one of embodiments 14-16, wherein the first wetness detection mechanism is disposed at a first detection zone on the substrate and wherein the wetness detection system further comprises: a second wetness detection mechanism disposed at a second detection zone on the substrate, the second detection zone on the substrate being different from the first detection zone on the substrate, the second wetness detection mechanism being configured to detect wetness being a result of leakage from the absorbent article and being in electrical communication with the controller, and wherein the controller is configured to record activity of the second wetness detection mechanism.

Embodiment 18

The method of embodiment 17, wherein the first wetness detection mechanism and the second wetness detection mechanism are each configured to detect wetness electronically.

Embodiment 19

The method of embodiment 18, wherein the first wetness detection mechanism and the second wetness detection mechanism each comprise conductive threads.

Embodiment 20

The method of any one of embodiments 17-19, wherein the first detection zone on the substrate corresponds to a first location on the absorbent article selected from the group consisting of: a front end edge, a rear end edge, a first side edge, and a second side edge; and wherein the second detection zone on the substrate corresponds to a second location on the absorbent article selected from the group consisting of: the front end edge, the rear end edge, a first side edge, and a second side edge.

These and other modifications and variations to the present disclosure can be practiced by those of ordinary skill in the art, without departing from the spirit and scope of the present disclosure, which is more particularly set forth in the appended claims. In addition, it should be understood that elements of the various aspects can be interchanged both in whole and in part. Furthermore, those of ordinary skill in the art will appreciate that the foregoing description is by way of example only, and is not intended to limit the disclosure so further described in such appended claims.

What is claimed:

1. A garment configured for detecting leakage from an absorbent article underlying the garment, the garment comprising:
   a substrate; and
   a wetness detection system configured to detect wetness indicating leakage from the absorbent article, the wetness detection system comprising:
      a first wetness detection mechanism disposed at a first detection zone on the substrate, the first detection zone corresponding to a first location on the absorbent article of interest to be monitored for leakage from the absorbent article; and
      a second wetness detection mechanism disposed at a second detection zone on the substrate, the second detection zone corresponding to a second location on the absorbent article of interest to be monitored for leakage from the absorbent article, the second detection zone being different than the first detection zone.

2. The garment of claim 1, wherein the wetness detection system further comprises:

a controller in electrical communication with the first wetness detection mechanism and the second wetness detection mechanism.

3. The garment of claim 2, wherein the first wetness detection mechanism and the second wetness detection mechanism are each configured to detect wetness electronically.

4. The garment of claim 3, wherein the first wetness detection mechanism and the second wetness detection mechanism each comprise conductive thread.

5. The garment of claim 2, wherein the wetness detection system further comprises a power source.

6. The garment of claim 2, wherein the controller is configured to be in electrical communication with a computer.

7. The garment of claim 1, wherein the first location on the absorbent article is selected from the group consisting of: a front end edge, a rear end edge, a first side edge, and a second side edge.

8. The garment of claim 7, wherein the second location on the absorbent article is selected from the group consisting of: the front end edge, the rear end edge, the first side edge, and the second side edge.

9. The garment of claim 8, wherein the wetness detection system further comprises a third wetness detection mechanism disposed at a third detection zone on the substrate, the third detection zone on the substrate being different than the first detection zone and the second detection zone on the substrate, the third detection zone on the substrate corresponding to a third location on the absorbent article of interest to be monitored for leakage from the absorbent article, the third location being selected from the group consisting of: the front end edge, the rear end edge, the first side edge, and the second side edge.

10. A garment configured for detecting leakage from an absorbent article underlying the garment, the garment comprising:
    a substrate; and
    a wetness detection system configured to detect wetness indicating leakage from the absorbent article, the wetness detection system comprising:
        a first wetness detection mechanism disposed at a first detection zone on the substrate, the first detection zone on the substrate corresponds to a first location on the absorbent article of interest to be monitored for leakage from the absorbent article, the first location being selected from the group consisting of: a front end edge, a rear end edge, a first side edge, and a second side edge;
        a second wetness detection mechanism disposed at a second detection zone on the substrate, the second detection zone being different than the first detection zone and corresponding to a second location on the absorbent article of interest to be monitored for leakage from the absorbent article, the second location being selected from the group consisting of: the front end edge, the rear end edge, the first side edge, and the second side edge; and
        a controller in electrical communication with the first wetness detection mechanism and the second wetness detection mechanism, the first wetness detection mechanism and the second wetness detection mechanism each being configured to detect wetness electronically indicating leakage from the absorbent article.

11. The garment of claim 10, wherein the wetness detection system further comprises:
    a third wetness detection mechanism disposed at a third detection zone on the substrate, the third detection zone being different than the first detection zone and the second detection zone and corresponding to a third location on the absorbent article of interest to be monitored for leakage from the absorbent article, the third location being selected from the group consisting of: the front end edge, the rear end edge, the first side edge, and the second side edge; and wherein the third wetness detection mechanism is configured to detect wetness electronically.

12. The garment of claim 10, wherein the wetness detection system further comprises a power source.

13. The garment of claim 10, wherein the controller is configured to be in electrical communication with a computer, the computer being configured to monitor the activity of the first wetness detection mechanism and the second wetness detection mechanism over time.

14. A method of detecting leakage from an absorbent article, the method comprising:
    providing an absorbent article on a test subject;
    providing a garment including a wetness detection system configured to detect wetness indicating leakage from the absorbent article, the wetness detection system comprising:
        a first wetness detection mechanism, the first wetness detection mechanism disposed on the substrate and being configured to detect wetness being a result of leakage from the absorbent article; and
        a controller in electrical communication with the first wetness detection mechanism, the controller configured to record activity of the first wetness detection mechanism;
    applying the garment to the test subject such that the garment overlays the absorbent article on the test subject; and
    monitoring the wetness detection system to detect leakage from the absorbent article.

15. The method of claim 14, wherein the wetness detection system further comprises a computer in electrical communication with the controller, the computer including an output interface for monitoring the wetness detection system to detect leakage from the absorbent article.

16. The method of claim 15, wherein the computer is configured to record a location of leakage of the absorbent article and a time of leakage of the absorbent article based on monitoring the activity of the wetness detection system.

17. The method of claim 14, wherein the first wetness detection mechanism is disposed at a first detection zone on the substrate and wherein the wetness detection system further comprises:
    a second wetness detection mechanism disposed at a second detection zone on the substrate, the second detection zone on the substrate being different from the first detection zone on the substrate, the second wetness detection mechanism being configured to detect wetness being a result of leakage from the absorbent article and being in electrical communication with the controller, and wherein the controller is configured to record activity of the second wetness detection mechanism.

18. The method of claim 17, wherein the first wetness detection mechanism and the second wetness detection mechanism are each configured to detect wetness electronically.

19. The method of claim 18, wherein the first wetness detection mechanism and the second wetness detection mechanism each comprise conductive threads.

20. The method of claim 17, wherein the first detection zone on the substrate corresponds to a first location on the absorbent article selected from the group consisting of: a front end edge, a rear end edge, a first side edge, and a second side edge; and wherein the second detection zone on the substrate corresponds to a second location on the absorbent article selected from the group consisting of: the front end edge, the rear end edge, the first side edge, and the second side edge.

\* \* \* \* \*